(12) United States Patent
Pearce et al.

(10) Patent No.: US 9,340,766 B2
(45) Date of Patent: May 17, 2016

(54) METHOD AND DEVICES FOR IMPROVED OXYGEN PERMEABILITY IN MICROORGANISM STORAGE CONTAINERS

(75) Inventors: Jeremy D. Pearce, Bosham (GB); Anthony Robert Hoare, Rugby (GB); Mary Ann Carpenter, Littlehampton (GB)

(73) Assignee: BASF Corporation, Florham Park, NJ (US)

( * ) Notice: Subject to any disclaimer, the term of this patent is extended or adjusted under 35 U.S.C. 154(b) by 394 days.

(21) Appl. No.: 13/021,916

(22) Filed: Feb. 7, 2011

(65) Prior Publication Data

US 2011/0272408 A1    Nov. 10, 2011

Related U.S. Application Data

(60) Provisional application No. 61/302,228, filed on Feb. 8, 2010.

(51) Int. Cl.
*B65D 30/08* (2006.01)
*C12M 1/00* (2006.01)
*C12M 1/04* (2006.01)

(52) U.S. Cl.
CPC .............. *C12M 45/22* (2013.01); *C12M 23/14* (2013.01); *C12M 23/24* (2013.01); *C12M 23/52* (2013.01)

(58) Field of Classification Search
CPC ...... B65D 33/01; B65D 77/225; B65D 31/04; B65D 33/02; B65D 81/18; B32B 27/32; B32B 7/02; C12M 23/14; C12M 23/24; C12M 45/22
USPC .................. 383/109, 102, 100, 101, 113; 229/117.35
See application file for complete search history.

(56) References Cited

U.S. PATENT DOCUMENTS

| 3,463,357 | A | * | 8/1969 | Maskell et al. | 222/94 |
|---|---|---|---|---|---|
| 3,625,348 | A | * | 12/1971 | Titchenal et al. | 206/484 |
| 4,132,594 | A | * | 1/1979 | Bank et al. | 435/2 |
| 4,368,766 | A | * | 1/1983 | Nomi | 383/80 |
| 4,454,945 | A | * | 6/1984 | Jabarin et al. | 206/524.3 |
| 4,579,223 | A | * | 4/1986 | Otsuka | B65D 81/268 206/204 |
| 4,876,146 | A | * | 10/1989 | Isaka et al. | 428/347 |
| 4,953,550 | A | * | 9/1990 | Dunshee | 607/114 |
| 4,956,209 | A | * | 9/1990 | Isaka et al. | 428/35.2 |
| 5,180,075 | A | * | 1/1993 | Montalbano | 229/103.11 |
| 6,068,898 | A | * | 5/2000 | Oyama | 428/35.2 |
| 7,066,337 | B2 | * | 6/2006 | Hsu | 210/452 |
| 2004/0191476 | A1 | * | 9/2004 | Wallen et al. | 428/138 |

(Continued)

FOREIGN PATENT DOCUMENTS

| EP | 0755875 A1 | 1/1997 |
|---|---|---|
| JP | 6054644 A | 3/1994 |

(Continued)

OTHER PUBLICATIONS

Translation of JP2000-354477, Dec. 26, 2000.*

(Continued)

*Primary Examiner* — Jes F Pascua
(74) *Attorney, Agent, or Firm* — Brinks Gilson & Lione

(57) ABSTRACT

The various embodiments disclosed herein relate to improved containers for transporting microorganisms and other living material. Certain embodiments include air-permeable bladders having an air-permeable inner wall and a stronger outer wall having perforations.

14 Claims, 3 Drawing Sheets

(56) References Cited

U.S. PATENT DOCUMENTS

| | | | |
|---|---|---|---|
| 2007/0164092 A1* | 7/2007 | Biundo | 229/117.3 |
| 2007/0248291 A1* | 10/2007 | Reeves et al. | 383/102 |
| 2009/0239009 A1 | 9/2009 | Tanaka | |
| 2013/0279829 A1* | 10/2013 | Goglio | B65D 33/01 383/45 |
| 2013/0279830 A1* | 10/2013 | Goglio | B65D 31/04 383/109 |

FOREIGN PATENT DOCUMENTS

| | | | |
|---|---|---|---|
| JP | 07033170 A * | 2/1995 | B65D 81/26 |
| JP | 2000 168834 A2 | 6/2000 | |
| JP | 2000354477 A | 12/2000 | |
| JP | 2009027944 A | 2/2009 | |
| KR | 20070114431 A | 12/2007 | |
| WO | WO0004131 A1 | 1/2000 | |

OTHER PUBLICATIONS

Machine translation of Japanese Document No. 7-33170. Translated on Aug. 18, 2014.*

International Search Report and Written Opinion issued in PCT/US2011/023940, mailed Jun. 10, 2011, 14 pages.

* cited by examiner

METHOD AND DEVICES FOR IMPROVED OXYGEN PERMEABILITY IN MICROORGANISM STORAGE CONTAINERS

CROSS-REFERENCE TO RELATED APPLICATIONS

This application claims priority to U.S. Provisional Application 61/302,228, filed Feb. 8, 2010, which is hereby incorporated herein by reference in its entirety.

FIELD OF THE INVENTION

Various embodiments disclosed herein relate to an improved oxygen-permeable container for storing and transporting microorganisms. More specifically, certain embodiments relate to a container having a thin inner wall and an outer wall having perforations.

BACKGROUND OF THE INVENTION

Liquid rhizobium inoculants have become widely available in recent years. The inoculants are predominantly packaged for sale and shipping in "bag-in-box" ("BIB") containers, which generally consist of a plastic bag or bladder positioned within a cardboard box. For illustrative purposes, it is understood that BIB containers are used for storing products such as wine and fruit juices.

During transport and storage of liquid inoculants, it is beneficial that the number of viable cells remain high and also that the rhizobium survive when applied to the seed prior to planting. Liquid rhizobial inoculants are not dormant products—the microbial cells are actively respiring, leading to a demand for oxygen. As a result, inoculants packaging must have oxygen permeability. Other microorganisms also require packaging that has oxygen permeability for purposes of storage and transport.

Known BIB containers for packaging liquid rhizobium inoculants use bags made of low density polyethylene ("LDPE") or related variants such as very low density polyethylene ("VLDPE"). These films are considered to be non-barrier films. That is, they are permeable to oxygen and carbon dioxide. The bladders used in these BIB containers are generally made of single layer films or two-ply films made up of two films that are both made of the same material, which is typically impermeable to liquid.

There is a need in the art for improved packaging for liquid rhizobium inoculants and other microorganisms.

BRIEF SUMMARY OF THE INVENTION

Disclosed herein are various oxygen-permeable bladder configurations for storing and transporting living material, including microorganisms.

In Example 1, an oxygen-permeable bladder comprises two walls coupled to each other along each outer edge of the two walls. Each of the two walls comprises a first film and a second film. The first film defines an inner wall of the bladder and comprises a thin, non-barrier flexible film. The second film is disposed adjacent to an outer surface of the first film and comprises a plurality of perforations.

Example 2 relates to the bladder according to Example 1, wherein the first film has an oxygen permeability of at least 5,500 cc/m$^2$/day.

Example 3 relates to the bladder according to Example 1, wherein one of the two walls comprises a spout extending from the one of the two walls, the spout defining an opening in fluid communication with an inner cavity of the bladder.

Example 4 relates to the bladder according to Example 3 and further comprises a cover configured to be coupleable to the spout.

Example 5 relates to the bladder according to Example 1, wherein the first film has a thickness ranging from about 15 μm to about 90 μm.

Example 6 relates to the bladder according to Example 1, wherein the first film comprises polyethylene or polypropylene.

Example 7 relates to the bladder according to Example 1, wherein the second film is mechanically stronger and more puncture resistant than the first film.

Example 8 relates to the bladder according to Example 1, wherein the second film has a thickness ranging from about 40 μm to about 80 μm.

Example 9 relates to the bladder according to Example 1, wherein the second film comprises polyester, polyethylene, polypropylene, or polyamide.

Example 10 relates to the bladder according to Example 1, wherein each of the plurality of perforations has a diameter ranging from about 0.1 mm to about 3 mm.

Example 11 relates to the bladder according to Example 1, wherein the first and second films are only bonded to each other along each outer edge of the two walls.

Example 12 relates to the bladder according to Example 1, wherein the bladder is configured to be disposed within an external container.

In Example 13, an oxygen-permeable bladder comprises at least one wall. The at least one wall comprises an inner oxygen-permeable film, an outer perforated film, and a bonded coupling. The inner oxygen-permeable film comprises a non-barrier flexible film. The outer perforated film is disposed adjacent to but not coupled along a substantial length of the outer perforated film with the inner oxygen-permeable film. The bonded coupling is configured to bond the inner oxygen-permeable film to the outer perforated film and is positioned around an outer portion of the at least one wall.

Example 14 relates to the bladder according to Example 13, wherein the inner oxygen-permeable film has an oxygen permeability of at least 5,500 cc/m$^2$/day.

Example 15 relates to the bladder according to Example 13, wherein one of the at least one walls comprises a spout and a cover. The spout is associated with the one of the at least one walls and defines an opening in fluid communication with an inner cavity of the bladder. The cover is configured to be coupleable to the spout.

Example 16 relates to the bladder according to Example 13, wherein the outer perforated film is mechanically stronger than the inner oxygen-permeable film.

In Example 17, a container for transporting live microorganisms comprises a substantially rigid external container and an oxygen-permeable bladder configured to be disposed within the substantially rigid external container. The oxygen-permeable bladder comprises an inner film and an outer film. The inner film comprises a non-barrier flexible film having a thickness ranging from about 15 μm to about 100 μm. The outer film is adjacent to the inner film and comprises a plurality of perforations. In addition, the outer film is bonded to the inner film solely along four outer edges of the outer film.

Example 18 relates to the bladder according to Example 17, wherein the inner film has an oxygen permeability of at least 5,500 cc/m$^2$/day.

Example 19 relates to the bladder according to Example 17, wherein the outer film is mechanically stronger than the inner film.

Example 20 relates to the bladder according to Example 17, wherein the bladder further comprises a spout associated with the bladder.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

Various embodiments disclosed herein relate to improved BIB containers for microorganisms, including liquid rhizobium inoculants, and related methods of making such containers. The embodiments include containers having bladders with increased oxygen permeability, which can improve the supply of oxygen to the microorganism, thereby resulting in better storage viability and subsequent efficacy of the microorganisms when applied. Generally, the various bladder embodiments disclosed herein have twin-ply walls, with each wall having two un-bonded films: an inner film and an outer perforated film.

Figure 1A:
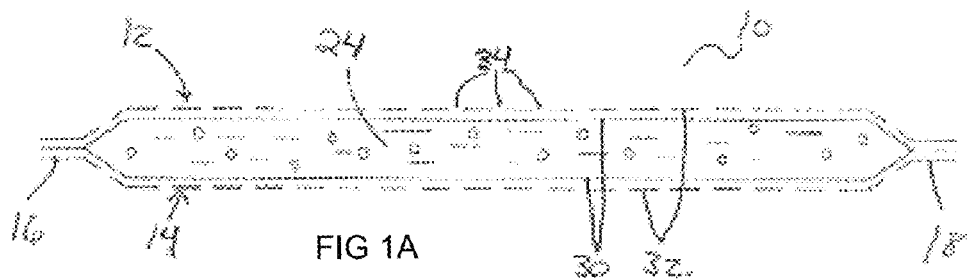
FIG. 1A is a schematic side view of a oxygen-permeable bladder, according to one embodiment.
Figure 1B:
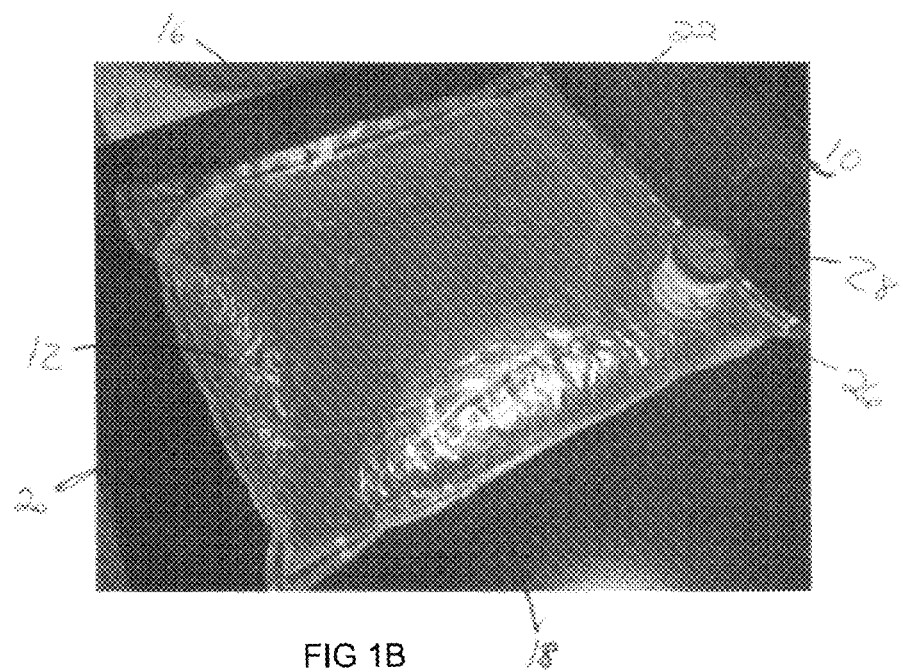
FIG. 1B is a perspective view of the bladder of FIG. 1A.

FIGS. 1A and 1B depict one embodiment of a permeable container 10 for use in a BIB container. The structure of this container 10 is the most common structure for bladders used in BIB containers. That is, the container 10 has two walls 12, 14 that are fixed, bonded, adhered, or otherwise attached to each other along each of the four edges 16, 18, 20, 22 (as best shown in FIG. 1B), thereby defining the inner cavity 24 of the container 10. According to one embodiment, the two walls 12, 14 are bonded together at the edges 16, 18, 20, 22 using a heat process. Alternatively, the walls 12, 14 can be bonded together at the edges 16, 18, 20, 22 using an adhesive. Alternatively, any known process or composition can be used to attach the two walls 12, 14 together. In a further alternative, the container can be formed by any known configuration that results in a container having an inner cavity and twin-ply oxygen-permeable walls according to any of the various embodiments disclosed herein. As best shown in FIG. 1B, the container 10 can also have a spout 26 disposed on the container 10 to provide fluid access to the inner cavity 24. The spout 26 can also have a cap 28 positioned on the spout 26.

In accordance with one embodiment, each of the walls 12, 14 is a "two-ply" or "twin-ply" wall. That is, each has an inner film 30 and an outer film 32. The two films 30, 32 are not physically bonded or otherwise attached to each other along the length of the cavity 24. Instead, the films 30, 32 are simply positioned adjacent to or in contact with each other in an un-bonded or unattached fashion and are only bonded to each other at the edges 16, 18, 20, 22 as described above.

The inner film 30, according to one implementation, is a thin film that has high oxygen permeability. The film 30 can be a lightweight, highly breathable film. According to one embodiment, the film 30 is thinner and thus has less strength—and hence is more breathable—than that required in known twin-ply containers. In one implementation, the inner film 30 is made of a mixture of high density polyethylene ("HDPE") and ultra low density polyethylene (ULDPE"). Alternatively, the inner film 30 can be made of various types of polyethylene, including, but not limited to, any one or more of HDPE, medium density polyethylene ("MDPE"), low density polyethylene ("LDPE"), very low density polyethylene ("VLDPE"), ULDPE, linear low density polyethylene ("LLDPE"), metallocene linear low density polyethylene ("mLLDPE"), and low pressure polyethylene ("LPPE"). According to another alternative, the inner film 30 can be made of a polypropylene. In a further alternative, the inner film can be any non-barrier flexible film, including any single film used in known BIB bladders, including those single films used in two-ply bladders. For purposes of this application, "non-barrier flexible film" means any thin, flexible polymeric film that is permeable to oxygen.

The inner film 30, in one implementation, is an extruded (or co-extruded) film. In this embodiment, the film 30 can be made using a standard extrusion process by first blending or mixing together the various components—such as any one or more of the exemplary components described above—in an extruder. The extruder then forms a homogenous film using those components. Alternatively, the inner film 30 can be made by any known extrusion process.

In accordance with one implementation, the inner film 30 can have a thickness ranging from about 15 μm to about 90 μm. Alternatively, the inner film 30 has a thickness of about 50 μm.

In one exemplary embodiment, the inner film 30 is a blend of a commercially-available polymer and HDPE. More specifically, the commercially-available polymer is sold under the brand name Dow Affinity PF 1140G, which is available from Dow Chemical Co., which is located in Midland, Mich. In one embodiment, the resulting inner film 30 is made up of about 82% of the Dow polymer and about 18% of the HDPE. As set forth in Table 1, which provides a comparison of the permeability of this particular inner film 30 to a conventional LDPE film, the inner film 30 has an oxygen permeability of about 5977 cc/m2/day.

TABLE 1

| Film type | Cc/m2/day |
|---|---|
| Inner Film (Dow Affinity PF 1140G)/HDPE | 5977 |
| Conventional film | 3300 |

The outer film 32, in accordance with one embodiment, is a film having multiple perforations 30. The outer film 32 can be made of a polyester/polyethylene film in which the film is made up a mixture of 24% polyester and 76% polyethylene by thickness. In addition to polyester and polyethylene, further non-limiting examples of materials include polypropylene and polyamide. Alternatively, the outer film 32 can be made of any heat-sealable laminated film. A heat-sealable film can be made of materials such as LDPE or ULDPE. In a further alternative, the outer film 32 can be made of any flexible film, including, for example, films made of polyester. In one specific exemplary embodiment, the outer film 32 is a mixture of polyester and polyethylene, which is commercially available as Corapan PS/LLE 12+40 from Corapack, which is located in Brenna, Italy, in which the polyester makes up about 24% of the film and the polyethylene makes up about 76% of the film.

According to one implementation, the outer film 32 is a laminated film that can be formed using a lamination process. In one example, a layer of polyester and a layer of polyethylene are first formed and then are laminated together. In one embodiment, the two layers are laminated together using an adhesive layer between them. Alternatively, the two layers can be laminated together using any known process. According to one specific implementation, the polyethylene layer is formed using a known blown film process. Alternatively, the polyethylene layer can be formed using any known process. The polyester layer can be formed using a known cast film process. Alternatively, the polyester layer can be formed using any known process.

In one embodiment, the outer film 32 has a thickness ranging from about 40 μm to about 80 μm. Alternatively, the outer film 32 has a thickness of about 52 μm. Each of the perforations can have a diameter ranging from about 0.1 mm to about 3 mm at a pitch ranging from about 5 mm to about 30 mm. Alternatively, the perforations can have a diameter of about 1 mm holes at a pitch of from about 10 to 20 mm.

The outer film 32 is mechanically stronger than the inner film 30. In accordance with one implementation, the outer film 32 can be mechanically stronger than films used in known BIB bladders while having higher oxygen permeability because of the perforations. That is, the permeability characteristics of the outer film 32 resulting from the perforations are independent of the mechanical properties of the film 32, thereby resulting in a perforated outer film 32 that is mechanically strong yet highly permeable to oxygen. Thus, in certain embodiments, the outer film 32 provides mechanical strength and puncture resistance to the container 10. This strength makes it possible for the inner film 30 to be made of the lightweight, highly breathable film having less strength, as described above.

Because of the properties of the two films 30, 32, various versions of the twin-ply wall embodiments described herein having both high oxygen permeability while also having sufficient strength to retain the liquid inoculants within the container 10. While the various known bladders have oxygen permeability, most have only a single-layer film or two layers that are physically bonded together to produce a single layer. These single-layer films sacrifice permeability for the thickness required to achieve the amount of strength necessary to contain liquids without breaking or being physically compromised in some fashion. In the various embodiments disclosed herein, the breathable, highly-permeable thin inner film combines with the highly-permeable but mechanically strong perforated outer film that is disposed next to but not bonded or physically joined to the inner film to create a highly permeable but mechanically strong wall that can be used to contain liquids containing microorganisms.

The various twin-ply wall embodiments having the inner and outer films as disclosed herein have, according to one embodiment, greater oxygen permeability than the conventional bladders known in the art. According to one embodiment, the two films 30, 32 create a twin-ply wall having an overall oxygen permeability ranging from about 4,000 cc/m$^2$/day to about 12,000 cc/m$^2$/day. Alternatively, the resulting twin-ply wall has an overall oxygen permeability of about 6,000 cc/m$^2$/day. Given that the permeability of a particular known conventional twin-ply bladder (which was constructed using two pieces of the same LDPE film, commercially available as FlexiOne™ 27 from Scholle Packaging Inc., which is located in Northlake, Ill.) is about 1,650 cc/m$^2$/day (as calculated using the standard method for determination of permeability set forth as ASTM #F1927-28, performed by Packaging Industry Research Association in Leatherhead, Surrey in England), this particular twin-ply embodiment having a permeability of about 6,000 cc/m$^2$/day exhibits permeability that is 363% greater than the known bladder.

Figure 1C:
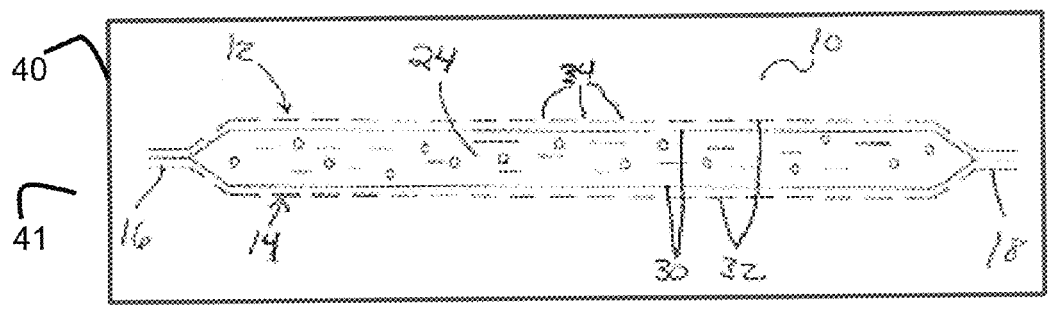
FIG. 1C. A schematic side view of an oxygen-permeable bladder inside of an external container, such as a "bag-in box" container, in accordance with one embodiment of the present invention.

It is understood that the various permeable container or bladder embodiments as described herein are, in certain implementations, positioned inside an external container (thereby resulting in a container have an external container and a bladder or permeable container disposed within the external container—a configuration typically referred to as a bag-in-box container as discussed above). In these implementations, the external container can be any known external container for use in BIB containers. For example, as shown in FIG. 1C, container 10 has two walls 12, 14, formed from inner film 30 and outer film 32 with perforations 34, are fixed, bonded, adhered, or otherwise attached to each other along edges 16, 18 to define inner cavity 24. The container 10 is inside rigid container 40 to form a BIB container 41. In one exemplary embodiment, the external container is a substantially rigid cardboard box. Alternatively, any other known external container is contemplated.

EXAMPLES

Example 1

Stability of *B. japonicum* in Containers at 7° C.

Figure 2:
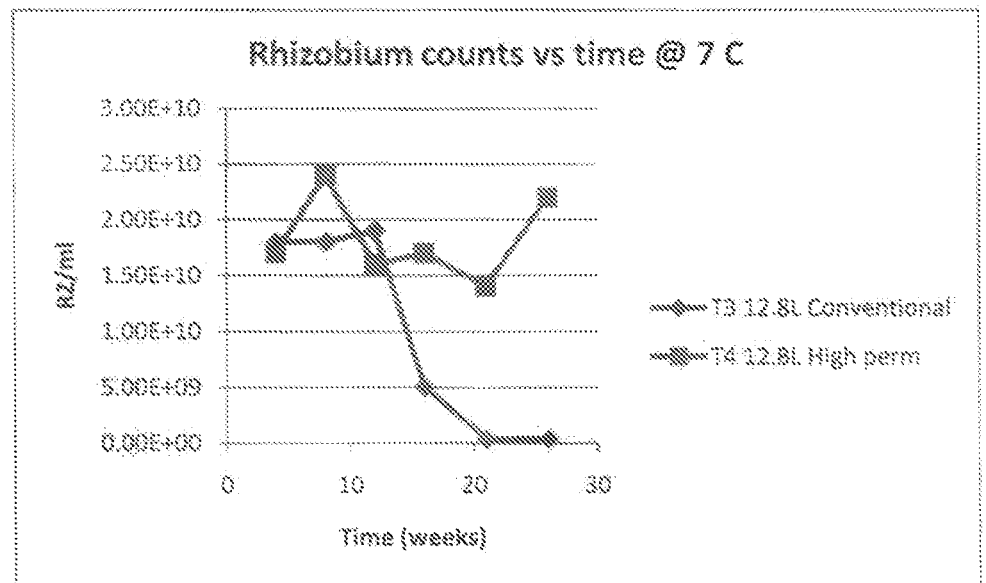
FIG. 2 is a line graph comparing the viability over time at 7° C. of microorganisms in a commercially-available bladder in comparison to a twin-ply bladder according to one embodiment.
Figure 3:
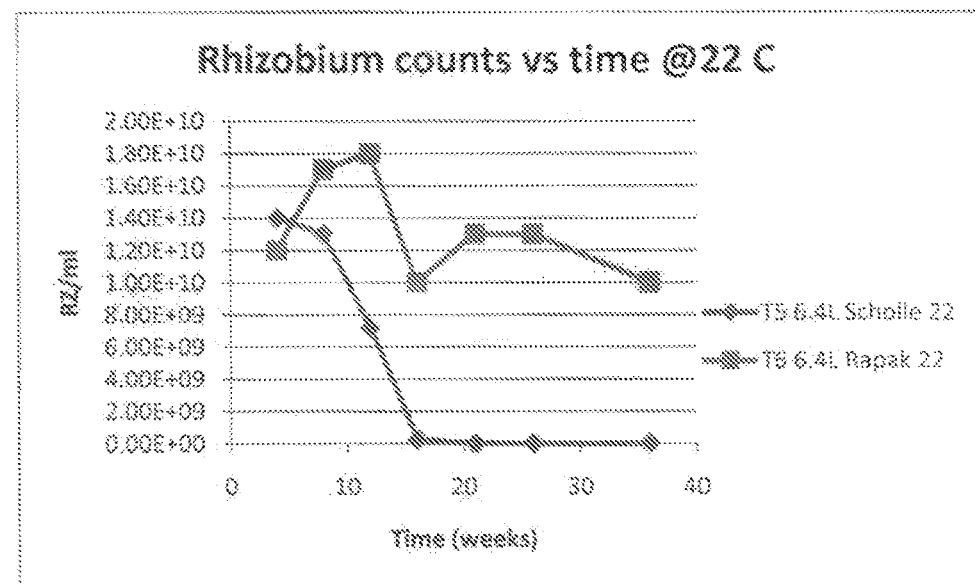
FIG. 3 is a line graph comparing the viability over time at 22° C. of microorganisms in a commercially-available bladder in comparison to a twin-ply bladder according to one embodiment.
Figure 4:
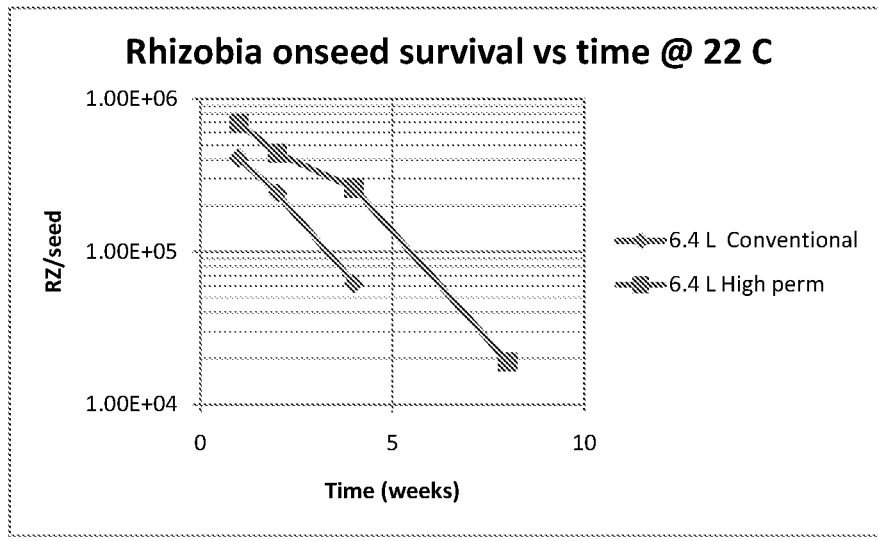
FIG. 4 is a line graph comparing the survivability over time at 22° C. of microorganisms on seed after storage in a commercially-available bladder in comparison to a twin-ply bladder according to one embodiment.
Figure 5:
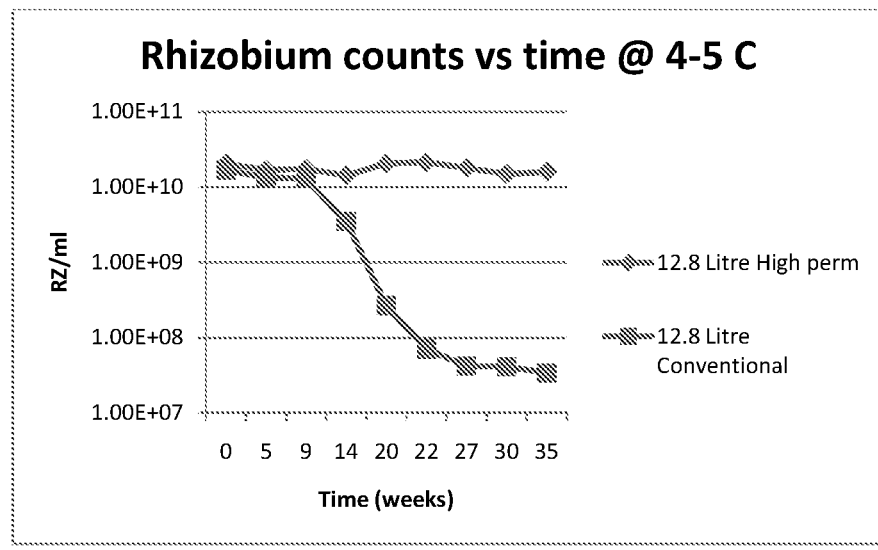
FIG. 5 is a line graph comparing the viability over time at 4° to 5° C. of microorganisms in a commercially-available bladder in comparison to a twin-ply bladder according to one embodiment.

Two 12.4 liter samples of fermented *Bradyrhizobium japonicum* broth were packaged into two different bladders. One sample was packaged in the same conventional polyethylene twin-ply bladder made of FlexiOne™ 27 as described above (labeled "Conventional" in FIG. 2), and a second sample was packaged in a particular embodiment of a twin-ply bladder (labeled "High perm" in FIG. 2). The twin-ply bladder embodiment had dimensions of 460×600 mm, an inner film of 50 μm thickness that was made of a blend of 82% Affinity 1140 G and 18% HDPE, and an outer film made of a perforated polyester/polyethylene film having 24% polyester and 76% polyethylene.

The material in both bladders was stored at 7° C. and samples were taken aseptically each month over the course of 6 months. The results are set forth in graphic form in FIG. 2.

As can be seen in the figure, after 12 weeks, the bacteria counts in the known, conventional BIB container showed a dramatic decline in viability. In contrast, the bacterial counts remained high in the twin-ply bladder embodiment up to 26 weeks.

Example 2

Stability of *B. japonicum* in Containers at 22° C.

Two 6.4 liter samples of fermented *B. japonicum* broth were packaged into two different bladders. One sample was packaged in the same bladder as described in Example 1 above (labeled "Conventional" in FIG. 3), and a second sample was packaged in the twin-ply bladder embodiment, also described in Example 1 (labeled "High perm" in FIG. 3).

The material in both bladders was stored at 22° C. and samples were taken aseptically each month over 6 months. The results are set forth in graphic form in FIG. 3. These results show that although there was a decline in bacterial counts in both the known bladder and the twin-ply bladder embodiment, the decline in the conventional packaging system was much greater than in the twin-ply embodiment.

Example 3

Stability of *B. japonicum* on Seed After Storage

The two samples from Example 2 were used in this experiment. After 5 weeks of storage at 22° C. as described above, each sample was applied separately to 500 grams of seed.

The numbers of surviving rhizobium in each batch were tested periodically as shown in FIG. 4. The results show that the on-seed survival of the rhizobium cells stored in the twin-ply bladder embodiment in Example 2 was higher than that of the rhizobium cells stored in the conventional bladder. In addition, the rhizobium cells stored in the twin-ply bladder embodiment stayed above the specification number (the minimum acceptable number of viable cells per seed prior to planting, as set forth in a Canadian regulation) of 100,000 cells per seed for over 5 weeks, in contrast to the cells stored in the conventional bladder, which dropped below the specification number in about 3 weeks. In other words, the time period between treating the seed and planting that treated seed in the field can be increased using the twin-ply bladder embodiment utilized in this Example.

Example 4

Stability of *B. japonicum* in Containers at 4-5° C.

Two 12.8 liter samples of fermented *B. japonicum* broth of the known strain 532C were packaged into two different bladders. One sample was packaged in the same bladder as described above in Examples 1 and 2 (labeled "Conventional" in FIG. 5), and a second sample was packaged in the twin-ply bladder embodiment as also described in Examples 1 and 2 (labeled "High perm" in FIG. 5).

The material in both bladders was stored at 4-5° C. and samples were taken aseptically each month over a period of 8 months. The results are set forth in graphic form in FIG. 5. As can be seen in the figure, the bacteria counts in the known, conventional BIB container began to decline at a significant rate starting at around 9 weeks. By 35 weeks, the bacterial counts in the twin-ply bladder embodiment remained high while the count decline in the conventional container was more than two logs greater.

Although the present invention has been described with reference to preferred embodiments, persons skilled in the art will recognize that changes may be made in form and detail without departing from the spirit and scope of the invention.

What is claimed is:

1. An oxygen-permeable bladder comprising two walls coupled to each other along each outer edge of the two walls, wherein each of the two walls comprises:

(a) a first film defining an inner wall of the bladder, the first film comprising a thin flexible film permeable to oxygen and carbon dioxide and impermeable to liquid; and (b) a second film disposed adjacent to an outer surface of the first film and comprising a plurality of perforations, wherein the first and second films are only bonded to each other along each outer edge of the two walls, and wherein each of the plurality of perforations has a diameter ranging from about 0.1 mm to about 3 mm, and wherein one of the two walls comprises a spout extending from the one of the two walls, the spout defining an opening in fluid communication with an inner cavity of the bladder.

2. The oxygen-permeable bladder of claim 1, wherein the first film has an oxygen permeability of at least 5,500 cc/$m^2$/day.

3. The oxygen-permeable bladder of claim 1, further comprising a cover configured to be coupleable to the spout.

4. The oxygen-permeable bladder of claim 3, wherein the first film has a thickness ranging from about 15 μm to about 90 μm.

5. The oxygen-permeable bladder of claim 3, wherein the first film comprises polyethylene or polypropylene.

6. The oxygen-permeable bladder of claim 3, wherein the second film has a thickness ranging from about 40 μm to about 80 μm.

7. The oxygen-permeable bladder of claim 3, wherein the second film comprises polyester, polyethylene, polypropylene, or polyamide.

8. The oxygen-permeable bladder of claim 1, wherein the first film has a thickness ranging from about 15 μm to about 90 μm.

9. The oxygen-permeable bladder of claim 1, wherein the first film comprises polyethylene or polypropylene.

10. The oxygen-permeable bladder of claim 1, wherein the second film has a thickness ranging from about 40 μm to about 80 μm.

11. The oxygen-permeable bladder of claim 1, wherein the second film comprises polyester, polyethylene, polypropylene, or polyamide.

12. A container for transporting live microorganisms, the container comprising: (a) a substantially rigid external container; and (b) an oxygen-permeable bladder configured to be disposed within the substantially rigid external container, the bladder comprising (i) an inner film comprising a flexible film permeable to oxygen and carbon dioxide and impermeable to liquid and having a thickness ranging from about 15 μm to about 100 μm; and (ii) an outer film adjacent to the inner film, the outer film comprising a plurality of perforations, wherein the outer film is bonded to the inner film solely along four outer edges of the outer film, and wherein each of the plurality of perforations has a diameter ranging from about 0.1 mm to about 3 mm.

13. The container of claim 12, wherein the inner film has an oxygen permeability of at least 5,500 cc/$m^2$/day.

14. The container of claim 12, wherein the bladder further comprises a spout associated with the bladder.

* * * * *